United States Patent [19]
Van Alst

[11] Patent Number: 5,414,749
[45] Date of Patent: May 9, 1995

[54] X-RAY FILM HOLDER WITH A COLLISION PREVENTIVE HOOD

[75] Inventor: Josephus A. M. Van Alst, Eindhoven, Netherlands

[73] Assignee: U.S. Philips Corporation, New York, N.Y.

[21] Appl. No.: 296,259

[22] Filed: Aug. 25, 1994

Related U.S. Application Data

[63] Continuation of Ser. No. 101,158, Aug. 3, 1993.

[30] Foreign Application Priority Data

Aug. 5, 1992 [EP] European Pat. Off. ............ 92202417

[51] Int. Cl.6 .............................................. G03B 42/02
[52] U.S. Cl. ...................................... 378/172; 378/173
[58] Field of Search ........................ 378/172, 173, 174

[56] References Cited

FOREIGN PATENT DOCUMENTS 967931 12/1957 Germany .

Primary Examiner—Craig E. Church
Attorney, Agent, or Firm—Jack D. Slobod

[57] ABSTRACT

A collision preventive hood is provided for use with an x-ray film holder having removable film cassettes. Adequate collision protection is achieved by providing a collision preventive hood with side sections that can be folded back or slid inside when the film cassettes are removed.

8 Claims, 2 Drawing Sheets

X-RAY FILM HOLDER WITH A COLLISION PREVENTIVE HOOD

This is a continuation of application Ser. No. 08/101,158, filed Aug. 3, 1993.

BACKGROUND OF THE INVENTION

1. Field of the Invention

The invention pertains to an x-ray film holder provided with a collision preventive hood. The invention also relates to an x-ray examination apparatus equipped with an x-ray film holder provided with a collision preventive hood.

2. Description of the Related Art

An x-ray film holder of said kind has been described in the German Patentschrift DE 967 931.

An x-ray film holder as described in the cited reference is equipped with a collision preventive hood that covers the film holder. Upon a collision of said hood with e.g. a patient, the hood is depressed and consequently, a switch is activated so that power supply to a motor driving the motion of the x-ray film holder is interrupted, and consequently the motion of the film holder is stopped. The collision preventive hood that is employed in the known x-ray film holder has fixed dimensions, so that said collision preventive device is unsatisfactory for use with a film holder having removable film cassettes.

SUMMARY OF THE INVENTION

It is inter alia an object of the invention to provide collision preventive means for an x-ray film holder having removable parts.

An x-ray film holder in accordance with the invention is characterised in that the collision preventive hood comprises a plurality of sections that are mutually displaceable.

For providing collision prevention by means of a collision preventive hood for an x-ray film holder with removable film cassettes, one should take into account, that the dimensions of the x-ray film holder having film cassettes attached to it are larger than the dimensions of said x-ray film holder having film cassettes removed from it. Because a collision preventive hood for an x-ray film holder in accordance with the invention comprises mutually displaceable sections it is achieved that the effective coveting area of said collision preventive hood is adaptive to the area to be covered; i.e. depending on e.g. film cassettes being attached to or removed from the x-ray film holder.

A preferred embodiment of an x-ray film holder in accordance with the invention is further characterised in that said sections can be folded back, relatively to one another.

When film cassettes are removed from the x-ray film holder, the area for which collision protection is to be provided is reduced because the size of the film holder with film cassettes attached to it is larger than the size of the film holder without film cassettes. In order to avoid undesired protrusion of the collision preventive hood, the effective dimensions of collision preventive hood are adjustable by folding back appropriate sections of the collision preventive hood. In so far as, if at all, motion of an x-ray examination apparatus provided with an x-ray film holder in accordance with the invention is restricted by the presence of the collision preventive hood, the restriction of motion is not restricted further by protruding parts of the collision preventive hood when film cassettes have been removed from the x-ray film holder.

A further preferred embodiment of an x-ray film holder in accordance with the invention is further characterised in that said plurality of sections comprises a central section and side sections that can be folded back with respect to said central section.

A collision preventive hood comprising side section that can be folded back with respect to a central section is particularly suitable for use with an x-ray film holder whereto film cassettes can be attached.

A further preferred embodiment of an x-ray film holder in accordance with the invention is further characterised in that said side sections are connected with said central section by means of hinges.

A collision preventive hood comprising sections that can be folded back by way of hinges has as an advantage that it is particularly simple to manufacture.

A further preferred embodiment of an x-ray film holder in accordance with the invention is further characterised in that said sections are sliding with respect to one another.

The motion of displaceable sections of a collision preventive hood for an x-ray film holder in accordance with the invention can be confined to a plane by devising slidingly displaceable sections.

A further preferred embodiment of an x-ray film holder in accordance with the invention is further characterised in that said plurality of sections comprises two sections that are sliding with respect to each other.

The number of parts from which a collision preventive hood for an x-ray film holder in accordance with the invention is composed can be limited by devising two slidingly displaceable sections.

A further preferred embodiment of an x-ray film holder in accordance with the invention is further characterised in that said plurality of sections comprises a central section and side sections that are sliding with respect to said central section.

It is achieved that comparatively small, and therefore light, parts of an collision preventive hood for an x-ray film holder in accordance with the invention are to displaced for adapting the collision preventive hood to the x-ray film holder having film cassettes attached to it or removed form it, by devising said collision preventive hood having a central section and side sections that are slidingly displaceable with respect to said central section. Said side sections having the purpose of covering film cassettes being attached to the x-ray film holder.

An x-ray examination apparatus in accordance with the invention preferably comprises an x-ray film holder having a collision preventive hood comprising sections that can be optionally folded back.

In an x-ray examination apparatus wherein an x-ray film holder can be placed in a park position when the x-ray film holder is not in use, or in an exposure position when an x-ray image on film is to be made, a patient is to be protected from receiving injury should as a consequence of motion of e.g. a carrier or any other part comprised in the x-ray examination apparatus, the x-ray film holder collide with the patient. The protection sought is preferably achieved by employing a collision preventive hood. However, in the park position usually film cassettes are removed from the film holder, whereas the x-ray film holder is equipped with film cassettes when the x-ray film holder is placed in the exposure position. To sustain collision protection, while not further restricting motion of an x-ray examination apparatus provided with an x-ray film holder in accordance with the invention, in so far as, if at all, motion of the x-ray apparatus is restricted by the presence of the collision preventive hood, when film cassettes have been removed from the film holder, the collision preventive hood is provided having sections that can be folded back when the film cassettes have been removed.

These and other aspects of the inventions will be elucidated on and become apparent with reference to the embodiments described hereinafter and with reference to the accompanying drawing.

DETAILED DESCRIPTION OF THE PREFERRED EMBODIMENTS

Figure 1:
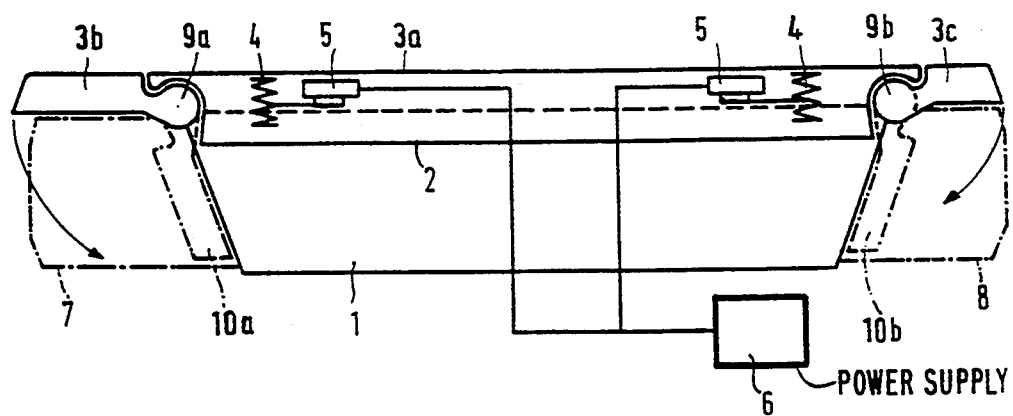
FIG. 1 shows a transparent side elevation of an embodiment of film holder in accordance with the invention.

FIG. 1 shows a transparent side elevation of an embodiment of a film holder in accordance with the invention. An x-ray film holder 1 is provided with a hood 2, that comprises three sections, viz. a central section 3a and two side sections 3b and 3c respectively. The collision preventive device comprises said hood together with springs 4 and switches 5. Should a collision occur, then the collision preventive hood depresses said springs so that switches 5 are opened and a power supply 6 is interrupted so that the motion of the x-ray film holder is stopped or reversed. Film cassettes 7 and 8 can be attached to the film holder in the positions indicated by phantom contours. The side sections 3b and 3c are connected to the central section 3a, by means of hinges 9a and 9b, respectively. In FIG. 1 the side sections are shown in the position for covering film cassettes being attached. When the film cassettes are removed from the film holder the side sections 3b and 3c can be folded into positions indicated by further phantom contours 10a and 10b, respectively. When the side sections have been folded back, unwanted protrusion of the collision preventive hood is avoided. Therefore, in so far as, if at all, motion of an x-ray examination apparatus provided with an x-ray film holder in accordance with the invention is restricted by the presence of the collision preventive hood, the restriction of motion is not restricted further by protruding parts of the collision preventive hood when film cassettes have been removed from the x-ray film holder.

Figure 2:
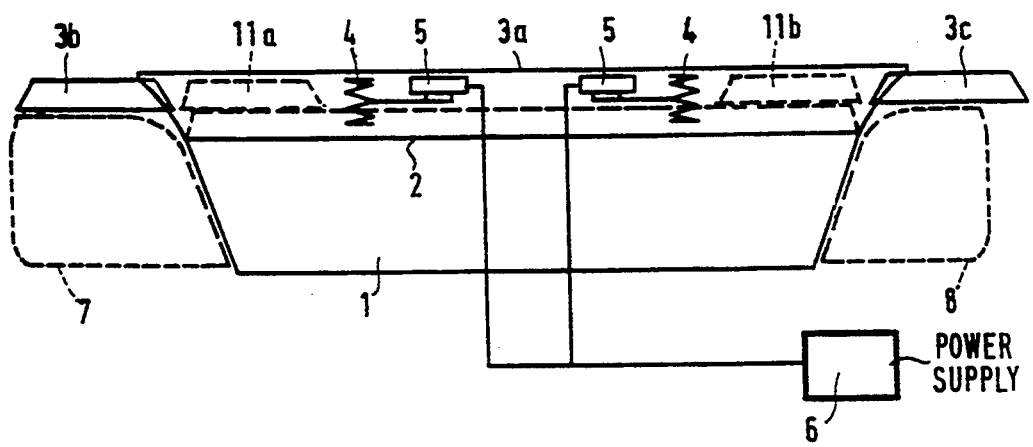
FIG. 2 shows a transparent side elevation of a further embodiment of film holder in accordance with the invention.

FIG. 2 shows a transparent side elevation of a further embodiment of film holder in accordance with the invention. The side sections 3b and 3c are slidingly mounted on the central section 3a. In FIG. 2, the side sections 3b and 3c are shown in positions for covering film cassettes 7 and 8 being attached to the x-ray film holder. The side sections 3b and 3c can be slidingly displaced to the positions 10a and 10b, respectively, as shown with phantom contours, when the film cassettes are removed. In the positions 10a and 10b, respectively, the side sections 3b and 3c do not protrude outside the x-ray film holder not having film cassette 7 and/or film cassettes 8 attached. Therefore, such a design contributes to reducing unwanted protrusion of the collision preventive hood.

Figure 3:
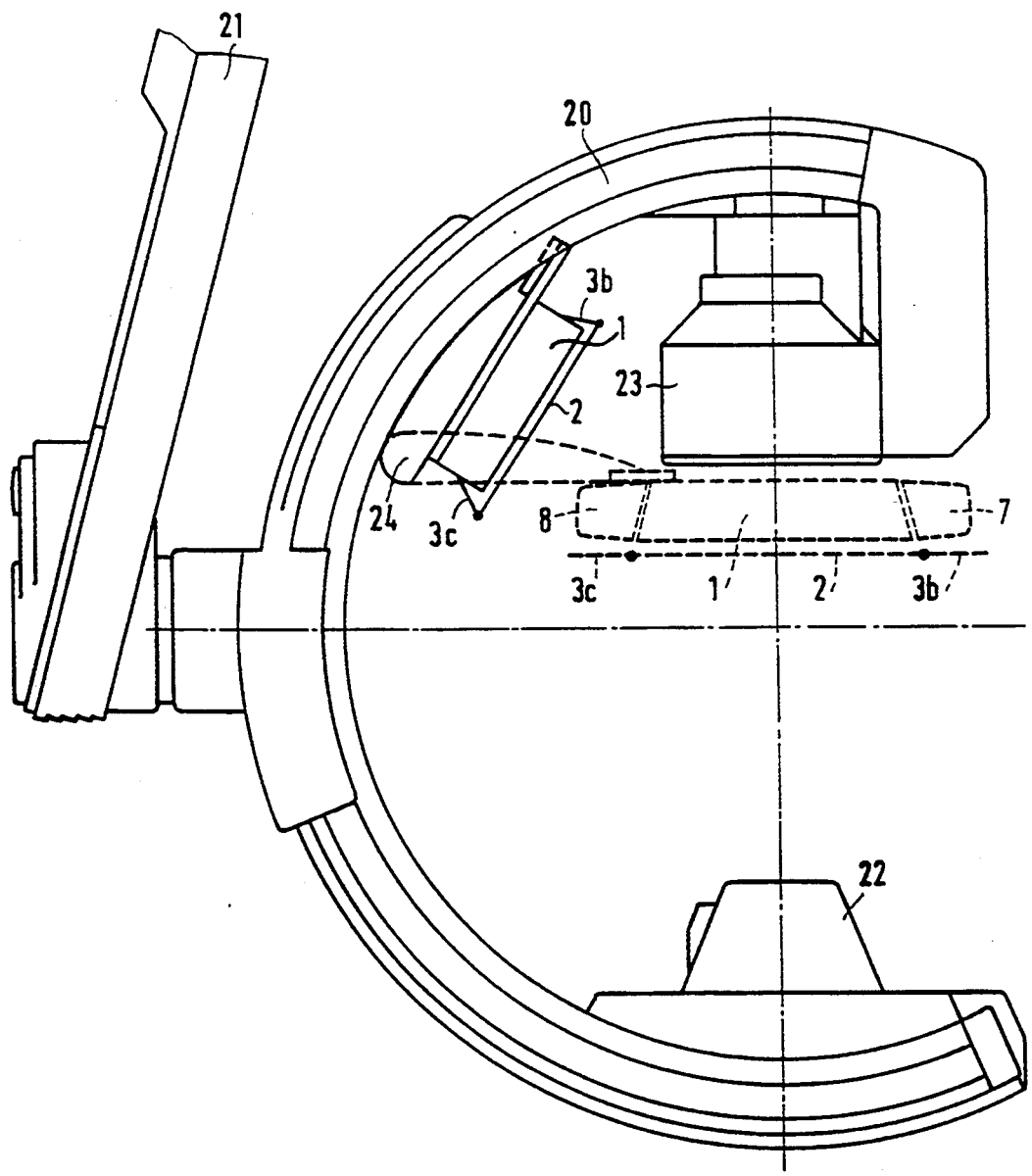
FIG. 3 shows a side elevation of an x-ray examination apparatus comprising an x-ray film holder in accordance with the invention.

FIG. 3 shows a side elevation of an x-ray examination apparatus comprising an x-ray film holder in accordance with the invention and comprising a carrier 20 mounted on a support 21, and supporting an x-ray source 22, an x-ray detector 23 and a frame 24. The x-ray film holder 1 is mounted on the frame 24. In FIG. 3 the film holder drawn in full lines, is shown in its park position, having film cassettes removed and having side sections 3b and 3c of the collision preventive hood 2 folded back. The x-ray film holder is placed in its park position when it is not needed for making an x-ray image on film. In dashed lines the film holder is moreover shown in its exposure position, having film cassettes 7 and 8 attached and having side sections 3b and 3c of the collision preventive hood 2 extended so as to cover the film cassettes. The x-ray film holder is placed in its exposure position with film cassettes attached to it when one or a plurality of x-ray image on film is to be made.

I claim:

1. An x-ray film holder adapted to be mounted on a frame supported by a moveable means of an X-ray examination apparatus, said x-ray film holder being provided with a collision preventive hood cooperating with switch means for in response to a collision of an object with said hood, interrupting a supply of power to said moveable means, characterised in that the collision preventive hood comprises a plurality of sections that are mutually displaceable.

2. An x-ray film holder as claimed in claim 1, further characterised in that said sections can be folded back, relatively to one another.

3. An x-ray film holder as claimed in claim 2, further charaeterised in that said plurality of sections comprises a central section and side sections that can be folded back with respect to said central section.

4. An x-ray film holder as claimed in claim 3, further characterised in that said side sections are connected with said central section by means of hinges.

5. An x-ray film holder as claimed in claim 1, further characterised in that said sections are sliding with respect to one another.

6. An x-ray film holder as claimed in claim 5, further characterised in that said plurality of sections comprises two sections that are sliding with respect to each other.

7. An x-ray film holder as claimed in claim 5, further characterised in that said plurality of sections comprises a central section and side sections that are sliding with respect to said central section.

8. An x-ray examination apparatus comprising a moveable means supporting an x-ray source and a frame, an x-ray film holder mounted on said frame for receiving x-ray film, which x-ray film holder is provided with a collision preventive hood cooperating with switch means for, in response to a collision of an object with said hood, interrupting a supply of power to said moveable means, said collision preventive hood comprising a plurality of sections that are mutually displaceable.

* * * * *